(12) United States Patent
Becker et al.

(10) Patent No.: US 8,329,606 B2
(45) Date of Patent: Dec. 11, 2012

(54) REGENERATION OF ZEOLITE CARBONYLATION CATALYSTS

(75) Inventors: Edo Johann Becker, Hull (GB); Evert Jan Ditzel, Goole (GB); Harry Kaiser, Leimen (DE); George Ernest Morris, Cottingham (GB); Mark Stephen Roberts, Beverley (GB); Stephan Andreas Schunk, Heidelberg (DE); Martin Smit, Bloemendaal (NL); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 102 days.

(21) Appl. No.: 12/735,122

(22) PCT Filed: Dec. 16, 2008

(86) PCT No.: PCT/GB2008/004137
§ 371 (c)(1),
(2), (4) Date: Aug. 11, 2010

(87) PCT Pub. No.: WO2009/077739
PCT Pub. Date: Jun. 25, 2009

(65) Prior Publication Data
US 2010/0311567 A1    Dec. 9, 2010

(30) Foreign Application Priority Data
Dec. 19, 2007  (EP) ..................................... 07254957

(51) Int. Cl.
*B01J 38/10*  (2006.01)
*C07C 51/12*  (2006.01)
(52) U.S. Cl. .......................................... 502/53; 562/519
(58) Field of Classification Search ........................ None
See application file for complete search history.

(56) References Cited

U.S. PATENT DOCUMENTS

| | | | |
|---|---|---|---|
| 3,825,613 A | 7/1974 | Kmecak et al. | |
| 4,423,272 A | 12/1983 | Forbus et al. | |
| 4,724,275 A * | 2/1988 | Hinnenkamp et al. | 585/733 |
| 5,151,393 A | 9/1992 | Harandi et al. | |
| 5,405,814 A | 4/1995 | Beech, Jr. et al. | |
| 6,632,765 B1 | 10/2003 | Chen | |
| 2007/0238897 A1 | 10/2007 | Cheung et al. | |

FOREIGN PATENT DOCUMENTS

| WO | WO 2005/105720 | 11/2005 |
|---|---|---|
| WO | WO 2007/128955 | 11/2007 |

OTHER PUBLICATIONS

International Search Report for PCT/GB2008/00004137, mailed May 11, 2009.
Written Opinion of the International Searching Authority for PCT/GB2008/00004137, mailed May 11, 2009.

\* cited by examiner

*Primary Examiner* — Paul A Zucker
(74) *Attorney, Agent, or Firm* — Nixon & Vanderhye (57) ABSTRACT

Process for the in-situ regeneration of a zeolite catalyst in a carbonylation process for the production of at least one of methyl acetate and acetic acid. The process is carried out by (a) contacting a carbonylatable reactant selected from methanol, dimethyl ether and dimethyl carbonate and carbon monoxide in a reactor with a zeolite catalyst and recovering a product stream containing at least one of methyl acetate and acetic acid from the reactor, (b) ceasing contact of the catalyst with the carbonylatable reactant, (c) regenerating the catalyst with a regenerating gas selected from hydrogen or a mixture of hydrogen and carbon monoxide at a temperature in the range 250 to 600 C, and (d) terminating the hydrogen regenerating step and resuming contact of the catalyst with the carbonylatable reactant and carbon monoxide.

15 Claims, 6 Drawing Sheets

REGENERATION OF ZEOLITE CARBONYLATION CATALYSTS

This application is the U.S. national phase of International Application No. PCT/GB2008/004137 filed 16 Dec. 2008, which designated the U.S. and claims priority to EP Application No. 07254957.9 filed 19 Dec. 2007, the entire contents of each of which are hereby incorporated by reference.

This invention relates to a process for the regeneration of zeolite carbonylation catalysts, such as mordenite, in a carbonylation process, and, in particular, in the carbonylation of methanol, dimethyl ether or dimethyl carbonate with carbon monoxide to produce at least one of methyl acetate and acetic acid.

BACKGROUND OF THE INVENTION

Zeolites, such as mordenite and ferrierite are known to be suitable for use as catalysts for the carbonylation of feedstocks such as methanol, dimethyl ether and dimethyl carbonate to produce the carbonylation products methyl acetate and/or acetic acid.

EP-A-0 596 632 describes a vapour phase process for the carbonylation of methanol to produce acetic acid in the presence of a modified mordenite catalyst at high temperatures and pressures.

WO 2005/105720 describes a process for production of a carboxylic acid and/or an ester or anhydride thereof by carbonylating an aliphatic alcohol or reactive derivative thereof with carbon monoxide in the substantial absence of halogens in the presence of a modified mordenite catalyst at a temperature in the range 250-600° C. and a pressure in the range 10 to 200 bar.

WO 2006/121778 describes a process for the production of a lower alkyl ester of a lower aliphatic carboxylic acid by carbonylating under substantially anhydrous conditions a lower alkyl ether with carbon monoxide in the presence of a mordenite or ferrierite catalyst.

'Heterogeneous catalysts for the direct, halide-free carbonylation of methanol' by Ellis et al, Studies in Surface Science and Catalysis, Vol. 111, pages 771-779, 1996, describes the catalyst preparation, performance and physical characterisation of Cu-mordenite compared to H-mordenite.

However, although the zeolites are highly effective carbonylation catalysts, it has been found that they undergo deactivation with time. Without wishing to be bound by theory, it is believed that loss in activity and/or selectivity is at least partly due to the formation of hydrocarbonaceous deposits (coke) which prevent access to the catalytically active sites of the zeolite. Thus, there remains a need for a method for treating a deactivated zeolite in order to at least partially restore activity whilst maintaining selectivity to acetyls product.

SUMMARY OF THE INVENTION

It has now been found that catalyst activity may be at least partially restored whilst maintaining selectivity to the desired acetyls product by treating a deactivated zeolite catalyst with hydrogen at elevated temperature and pressure.

Accordingly, the present invention provides a process for the in-situ regeneration of a zeolite catalyst in a carbonylation process for the production of at least one of methyl acetate and acetic acid which process comprises the steps:

(a) contacting a carbonylatable reactant selected from methanol, dimethyl ethyl and dimethyl carbonate and carbon monoxide in a reactor with a zeolite catalyst and recovering a product stream comprising at least one of methyl acetate and acetic acid from said reactor;

(b) ceasing contact of the catalyst with the carbonylatable reactant;

(c) regenerating the catalyst with a regenerating gas selected from hydrogen or a mixture of hydrogen and carbon monoxide at a temperature in the range 250 to 600° C.;

(d) terminating the hydrogen regenerating step and resuming contact of the catalyst with the carbonylatable reactant and carbon monoxide.

The zeolite which may be regenerated by the method of the present invention may be any zeolite which is effective to catalyse the carbonylation of methanol or dimethyl ether or dimethyl carbonate with carbon monoxide to produce at least one of methyl acetate and acetic acid. Zeolites suitable for such carbonylation reactions are those having at least one 8-member ring channel which is interconnected with a channel defined by a ring with greater than or equal to 8 members. Additionally, it has been found that to effectively catalyse carbonylation reactions of the present invention, the 8-membered ring should have a window size of at least 2.5 Angstroms by at least 3.6 Angstroms. Examples of such zeolites include zeolites of framework type MOR, FER and OFF, such as mordenite, ferrierite and offretite. The *Atlas of Zeolite Framework Types* (C. Baerlocher, W. M. Meier, D. H. Olson, 5$^{th}$ ed. Elsevier, Amsterdam, 2001) in conjunction with the web-based version (http://www.iza-structure.org/databases/) is a compendium of topological and structural details about zeolite frameworks, including the types of ring structures present in a zeolite and the dimensions of the channels defined by each ring type.

A particularly preferred zeolite for use in the present invention is a mordenite.

Preferably, the zeolite has a silica:$X_2O_3$ molar ratio of at least 5, wherein X is selected from aluminium, boron, iron, gallium and mixtures thereof. Where X is alumina, the silica:alumina molar ratio is suitably in the range 6 to 90:1, such as 10 to 40:1.

Zeolites are available from commercial sources, generally in the Na, $NH_4$ form or H-form of the zeolite. The $NH_4$ form can be converted to the acid (H-form) by known techniques, such as calcination at high temperature. The Na form can be converted to the acid (H-form) by converting first to an NH4 form by ion exchange with ammonium salts such as ammonium nitrate. Alternatively, zeolites may be synthesised using known techniques.

For use in a carbonylation process to produce acetic methyl acetate and/or acetic acid, the zeolite may be employed in the acid form (H-form) or it may be optionally ion-exchanged or otherwise loaded with one or more metals such as copper, silver, gold, nickel, iridium, rhodium, platinum, palladium or cobalt.

The metal loading on a zeolite may be expressed in terms of the fractional loading of the metal as gram atoms of metal per gram atom of aluminium in the zeolite. The metal loading can also be expressed as a mole percentage loading relative to aluminium in the zeolite through the relationship:

mol % Metal=(gram atoms Metal/gram atoms aluminium)×100

Thus, for example, a loading of 0.55 gram atoms of copper per aluminium in the zeolite equates to a 55 mol % loading of copper relative to aluminium in the zeolite.

Suitably, the metal loading may be in the range of 1 to 200 mol % relative to aluminium, for example, 5 to 120 mol %, such as 5 to 110 mol %.

The zeolite framework, may in addition to silicon and aluminium atoms, contain additional trivalent elements, such as boron, gallium and/or iron.

Where the zeolite contains at least one or more trivalent framework elements, the metal loading in the zeolite can be expressed in terms of the fractional loading of the metal as gram atoms of metal per gram atom of total trivalent elements in the zeolite. The metal loading can also be expressed as a mole percentage loading relative to total trivalent elements in the zeolite through the relationship:

mol % Metal=(gram atoms Metal/gram atoms of total trivalent elements)×100

In one embodiment of the present invention the zeolite to be regenerated is a mordenite in the H-form or a metal loaded mordenite such as a copper loaded mordenite or a silver loaded mordenite or a metal loaded mordenite containing additional trivalent elements in its framework such as boron, gallium and/or iron, preferably, gallium.

The regeneration process of the present invention is conducted 'in-situ'. By 'in-situ' is meant that the carbonylation reaction is ceased, the regeneration process is carried out and then the carbonylation reaction is restarted. In this manner it is not necessary to remove the zeolite catalyst from the carbonylation reactor.

To carry out the regeneration in-situ, contact of the catalyst with the carbonylatable reactant feed is ceased prior to the start of the regeneration.

In the regeneration step, the catalyst is contacted with a regenerating gas selected from hydrogen or a mixture of hydrogen and carbon monoxide.

Mixtures of hydrogen and carbon monoxide may be obtained from commercial suppliers of such mixtures and may contain small quantities of other inert constituents such as carbon dioxide and methane.

Where a mixture of hydrogen and carbon monoxide is used as the regenerating gas the hydrogen and carbon monoxide may each be fed into the reactor as a single feed stream but are preferably employed as a mixed feed stream.

Where the carbonylation process is carried out with carbon monoxide in the presence of hydrogen and the regenerating gas to be used is a mixture of hydrogen and carbon monoxide, it is not necessary to cease contact of catalyst with the carbon monoxide and hydrogen feed. However, for use in the regeneration step, the partial pressure of the hydrogen may be adjusted. Suitably, the partial pressure of hydrogen in the regenerating gas may be adjusted to be higher than the partial pressure of hydrogen used in the carbonylation process. If it is desired to use hydrogen alone as the regenerating gas, contact of the catalyst with the carbon monoxide feed may be ceased.

The regeneration of the catalyst is carried out at a temperature in the range 250 to 600° C., suitably in the range 300 to 500° C.

Where the catalyst bed is in the temperature range 250 to 600° C., the regenerating gas may be contacted with the catalyst.

A regeneration may be carried out at a different temperature to that used in the carbonylation reaction. Adjustment of the catalyst temperature may be carried out by any suitable means, such as, heat exchangers. Typically, the temperature used for the regeneration will be higher than that used in the carbonylation reaction. In such a case, the regenerating gas may be contacted with the catalyst whilst increasing the temperature of the catalyst from that used in the carbonylation reaction to the desired regenerating temperature.

Where the regenerating gas is hydrogen, the partial pressure of hydrogen may suitably be in the range 1 to 100 bar, such as 5 to 80 bar, for example, 10 to 70 bar.

The gas hourly space velocity (GHSV) of hydrogen may suitably be in the range 500 to 10,000 h$^{-1}$, such as 2000 to 8000 h$^{-1}$.

Where the regenerating gas is hydrogen in combination with carbon monoxide, the molar ratio of hydrogen:carbon monoxide may be in the range 20:1 to 1:10, such as 5:1 to 1:5.

Where a mixture of hydrogen and carbon monoxide is used as the regenerating gas, the partial pressure of carbon monoxide may be in the range 0.1 to 80 bar, such as 5 to 65 bar, for example 10 to 65 bar and the partial pressure of hydrogen may be in the range 0.1 to 99.9 bar, such as 5 to 80, for example 10 to 70 bar. Preferably, hydrogen is used at a partial pressure in the range, 10 to 70 bar, such as 20 to 40 bar in combination with a carbon monoxide partial pressure in the range, 5 to 65 bar such as 30 to 50 bar.

The total gas hourly space velocity (GHSV) of hydrogen and carbon monoxide may be in the range 500 to 10,000 h$^{-1}$, such as 2000 to 8000 h$^{-1}$.

The regeneration may be carried out at a total pressure in the range 1 to 100 bar, such as 1 to 80 bar. The total pressure used for the regeneration may be the same or different to that used in the carbonylation process, preferably the same.

Suitably, the regeneration is carried out at a temperature in the range 300 to 500° C. and at a total pressure in the range 1 to 80 bar.

The conditions under which a regeneration is carried out may be changed over the course of a regeneration. For example, the catalyst temperature may be adjusted, either by increasing the temperature or reducing the temperature, with the proviso that the temperature used is in the range 250 to 600° C.

The period over which the catalyst is contacted with the regenerating gas is chosen such that activity of the catalyst after regeneration is greater than the activity of the catalyst immediately prior to the start of the regeneration process. Typically, the contact period is in the order of hours, such as in the range 1 to 500 hours, for example 10 to 50 hours.

After regeneration of the catalyst has been completed, the carbonylation process is resumed by re-introducing the carbonylatable reactant feed, carbon monoxide and, if desired, hydrogen.

Prior to re-starting the carbonylation process, the reactor may be cooled to the desired carbonylation reaction temperature, by using, for example, an inert gas such as nitrogen.

Where the regenerating gas is a mixture of carbon monoxide and hydrogen, after use in the regeneration step, the mixture may be fed to a separate carbonylation reactor and used therein to carbonylate methanol, dimethyl ether or dimethyl carbonate.

Advantageously, the regeneration process of the present invention allows the activity of the catalyst to be at least partially restored without significant detrimental effect on selectivity to carbonylation product. Furthermore, multiple regenerations may be carried out during the course of a carbonylation process without significantly affecting the selectivity to carbonylation product. Thus, the regeneration step may be carried out once or it may be repeated multiple times during a carbonylation process. Suitably, regeneration is carried out twice in the carbonylation process.

Where multiple regenerations are carried out, each of the regenerations may be carried out under the same or different conditions to those employed in the first, a subsequent or a previous regeneration. For example, a regeneration may be carried out at a different catalyst temperature to that used in a subsequent or a previous regeneration. The composition of the regenerating gas may be changed. The regenerating gas used in one regeneration may be a mixture of hydrogen and carbon monoxide but in a subsequent or previous regeneration, the regenerating gas may be hydrogen only. The molar ratio of carbon monoxide:hydrogen used in one regeneration may be different to that used in a previous or subsequent regeneration.

The regeneration is carried out in the production of at least one of methyl acetate and acetic acid by the carbonylation of a carbonylatable reactant selected from dimethyl ether, dimethyl carbonate and methanol.

Where the carbonylatable reactant is dimethyl ether or dimethyl carbonate the carbonylation process is typically carried out by passing dimethyl ether or dimethyl carbonate, carbon monoxide and, if desired, hydrogen, through a fixed or fluidised bed of catalyst maintained at the required temperature, such as in the range 150 to 350° C., such as 250 to 350° C. The process is typically carried out under substantially anhydrous conditions, that is less than 2.5 wt % water in the dimethyl ether or dimethyl carbonate feed and at a total reaction pressure in the range 1 to 100 bar and a gas hourly space velocity in the range 500 to 40,000 $h^{-1}$.

Where the carbonylatable reactant is methanol the carbonylation process is typically carried by passing the methanol, carbon monoxide and, if desired, hydrogen through a fixed or fluidised bed of catalyst maintained at the required temperature, such as in the range 250 to 400° C., such as 275 to 350° C. The process is typically carried out at a total reaction pressure in the range 1 to 100 bar.

If the carbonylation reaction is to be conducted substantially in the absence of water it is preferred that the catalyst is dried prior to use. The catalyst may be dried, for example by heating to a temperature of 400 to 500° C.

Suitably, the catalyst is activated immediately before use in the carbonylation reaction by heating the zeolite at elevated temperature for at least one hour under flowing nitrogen, carbon monoxide, hydrogen or mixtures thereof.

The carbon monoxide employed in the carbonylation process may be substantially pure carbon monoxide, for example, carbon monoxide typically provided by suppliers of industrial gases, or it may contain impurities that do not interfere with the conversion of the reactant to the reaction products, such as nitrogen, helium, argon, methane and/or carbon dioxide.

The carbon monoxide feed may contain hydrogen. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide. The molar ratio of carbon monoxide:hydrogen may be in the range 1:3 to 15:1. The molar ratio of carbon monoxide to dimethyl ether or dimethyl carbonate may be in the range 1:1 to 99:1. The molar ratio of carbon monoxide to methanol is suitably in the range 1:1 to 60:1.

Where the carbonylatable reactant is dimethyl ether or dimethyl carbonate, the primary product of the carbonylation process is methyl acetate but small amounts of acetic acid may also be produced. The methyl acetate product can be removed in the form of a vapour and thereafter condensed to a liquid.

The methyl acetate may be recovered and sold as such or it may be forwarded to other chemical processes. Where the methyl acetate is recovered from the carbonylation reaction products, some or all of it may be hydrolysed to form acetic acid. Alternatively, the entire carbonylation reaction product may be passed to a hydrolysis stage and acetic acid separated thereafter. The hydrolysis may be carried out by known techniques such as reactive distillation in the presence of an acid catalyst.

Where the carbonylatable reactant is methanol, the product will be acetic acid but some methyl acetate may be formed.

The carbonylation process may be carried out as a continuous or a batch process, preferably a continuous process.

BRIEF DESCRIPTION OF THE DRAWINGS

The invention is further described with reference to the accompanying Figures, in which.

The invention is now illustrated with reference to the following Examples.

General Reaction Method 1

The carbonylation of dimethyl ether in the presence of a mordenite catalyst was carried out in a pressure flow reactor unit consisting of 16 identical reactors of the type described in WO 2005063372. Prior to the loading of a catalyst into the reactor, a ca. 5 cm bed of steatite of sieve fraction of 100-350 μm was placed in the respective catalyst holder. A ca. 5 cm zone of corundum of sieve fraction of 125-160 μm was placed on top of the steatite bed. On a dry mass basis (determined by loss on ignition of the relevant catalyst measured by heating the catalyst from room temperature to 600° C. at a ramp rate of approximately 30° C. per minute with an air flow of 1 l/min) a 0.625 g (ca. 1 ml) of a catalyst was then placed on top of the corundum bed. The catalyst was covered by a ca. 5 cm corundum bed of a particle size of 125-160 μm. A ca. 5 cm zone of steatite of sieve fraction of 100-350 μm was placed on top of the corundum bed. Every zone was concreted via hitting or vibrating to get a stable bed and a defined starting height of the catalyst zone. The catalyst was then pressurised to the desired reaction pressure of 70 bar with CO and $H_2$ at a molar ratio of 4:1 and a flow rate of 4 l/h. The catalyst was then heated at 0.5° C./min to a holding temperature of 220° C., where it was held for 3 hours. Subsequently the temperature was ramped to 300° C. at 0.5° C./min, and held at this temperature for 3 hours. The gas feed was then changed to a mixture of carbon monoxide hydrogen and dimethyl ether at a molar ratio of 71.9/18.0/10.1 and a flow rate of 4 l/h, with the dimethyl ether fed at 0.40 l/h as a vapour, to obtain a CO/$H_2$/dimethyl ether molar ratio of 71.9/18.0/10.1. Nitrogen gas was introduced at a variable rate of 0-50 ml/min to equalise the pressure swings between the 16 reactor exits. The exit stream from each reactor was passed to a gas chromatograph to determine the concentration of reactants and carbonylation products.

EXAMPLES 1 AND 2

Preparation of Catalyst A—H-Mordenite

Mordenite with a silica to alumina ratio of 20 (ex Süd-Chemie) was compacted with a powtec roller compactor at 250 bar using a total of 6 cycles and then crushed and sieved to a particle size fraction of 125 to 160 microns. 2.5 g of the sieved mordenite was then impregnated with 2780 µL of deionised water. After the impregnation the mordenite was left at ambient conditions on a shaker for 1 hour. The mordenite was then transferred to a forced convection oven (air as atmosphere) and heated to 80° C. for 20 hours. After drying the mordenite was calcined in air (with an air flow of 1 l/min) in a muffle oven (oven-volume=12 L) and heated at a ramp rate of 1° C./min to a temperature of 120° C. and then held at 120° C. for 180 minutes. The temperature was then increased by 1° C./min to 500° C. and held at 500° C. for 180 minutes. The mordenite was then cooled to room temperature in the muffle oven under dry air flow of 1 l/min. The mordenite was then gently pushed through a 160 µm sieve and sieved to obtain particles having a size in the range 125-160 µm.

Preparation of Catalyst B—Cu(55)-Mordenite

Mordenite with a silica to alumina ratio of 20 (ex Süd-Chemie) was compacted with a powtec roller compactor at 250 bar using a total of 6 cycles and then crushed and sieved to a particle size fraction of 125 to 160 microns. A solution of 448 µL copper (II) nitrate of concentration 4 mol/l diluted in 2332 µL of deionised $H_2O$ was used to impregnate 2.5 g of the sieved mordenite. After the impregnation the copper loaded mordenite was left at ambient conditions on a shaker for 1 hour. The copper loaded mordenite was then transferred to a forced convection oven (air as atmosphere) and heated to 80° C. for 20 hours. After drying the copper mordenite was calcined in air (with an air flow 1 l/min) in a muffle oven (oven-volume=12 L) and heated at a ramp rate of 1° C./min to a temperature of 120° C. and held at 120° C. for 180 minutes. The temperature was then increased by 1° C./min to 500° C. and held at 500° C. for 180 minutes. The copper mordenite was then cooled to room temperature in the muffle oven under dry air flow of 1 l/min. The copper mordenite was then gently pushed through a 160 µm sieve and sieved to obtain particles having a size in the range 125-160 µm. The mordenite had a copper loading of ca. 55 mole % relative to aluminium contained in the mordenite.

Preparation of Carbonylation Products and Regeneration with Hydrogen

In Examples 1 and 2 dimethyl ether was carbonylated to methyl acetate product. In Example 1, Catalyst A (H-mordenite) was used and in Example 2, Catalyst B (Cu-mordenite) was used. The carbonylation reactions were carried out using the apparatus and procedure described in General Reaction Method 1 above. Each reaction was allowed to continue for 107 hours under conditions of 300° C., 70 bar, a gas hourly space velocity (GHSV) of 4000 $h^{-1}$ and with a $CO/H_2/DME$ molar ratio in the total feed of 71.9/18.0/10.1. After 107 hours regeneration was carried out as follows:

The $CO/H_2/DME$ carbonylation feed was changed to $H_2$ fed at a GHSV of 4000 $h^{-1}$ at a total pressure of 70 bar. The catalysts were treated with flowing $H_2$ whilst increasing the temperature from 300° C. to 400° C. at a ramp rate of 1° C./min, followed by a dwell time at 400° C. of 10 hours under flowing $H_2$.

After the regeneration the reactors were cooled to the reaction temperature, 300° C., under $N_2$ fed at a GHSV of 4000 $h^{-1}$. At 123 hours the carbonylation reaction was re-started under conditions of 300° C., 70 bar total pressure and a GHSV of 4000 $h^{-1}$ and $CO/H_2/DME$ at a molar ratio of 71.8/18.0/10.2. The reaction was allowed to continue for a further 73 hours after which time, the catalysts were regenerated for a second time using the same conditions as were used in the first regeneration.

At 217 hours the carbonylation reaction was re-started under conditions of 300° C., 70 bar total pressure and a GHSV of 4000 $h^{-1}$ and $CO/H_2/DME$ of molar ratio 71.8/18.0/10.2. The reaction was allowed to continue for a further 73 hours.

Figure 1:
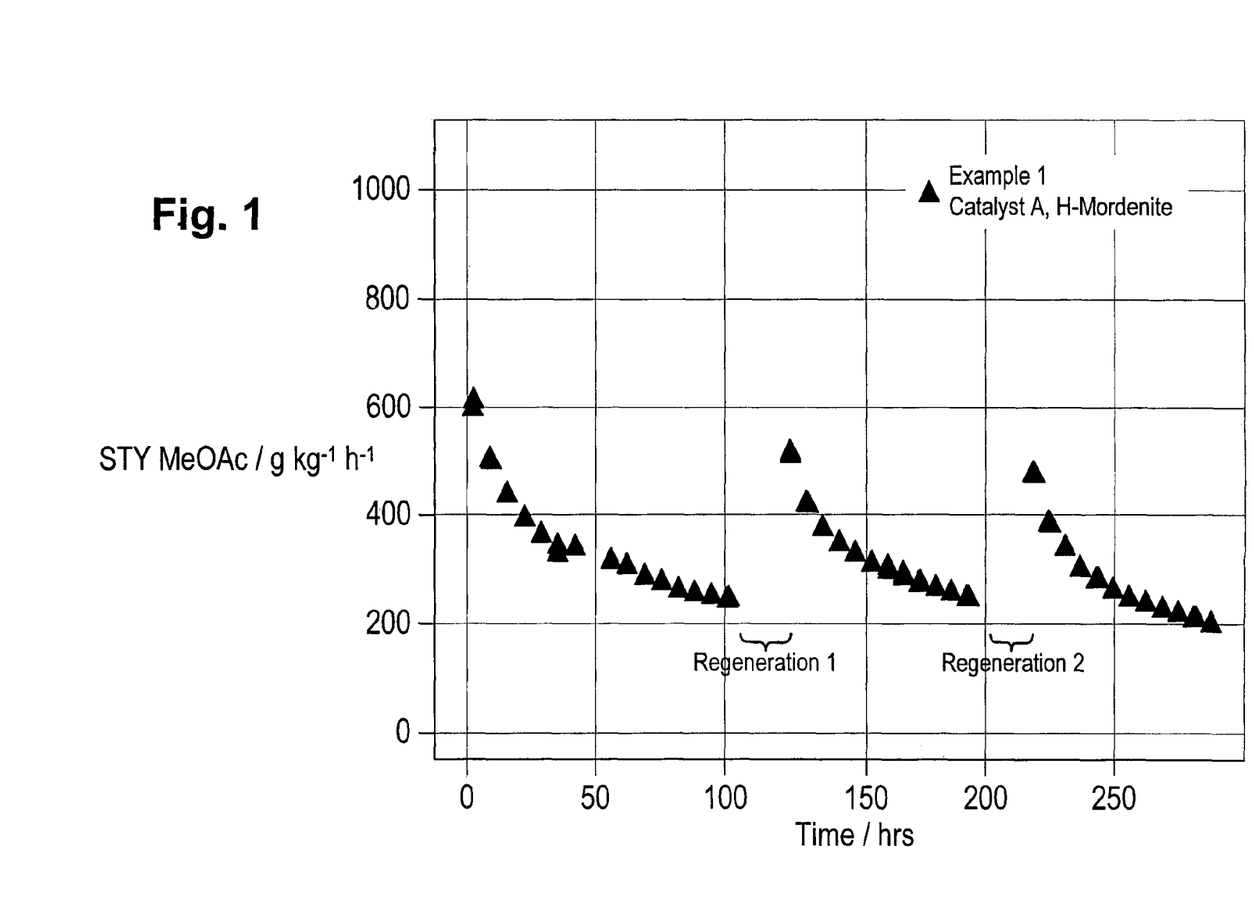
FIG. 1 depicts the STY to methyl acetate product in g $kg^{-1}$ $h^{-1}$ versus time on stream for H-mordenite catalyst before and after regeneration at 400° C. with hydrogen.
Figure 2:
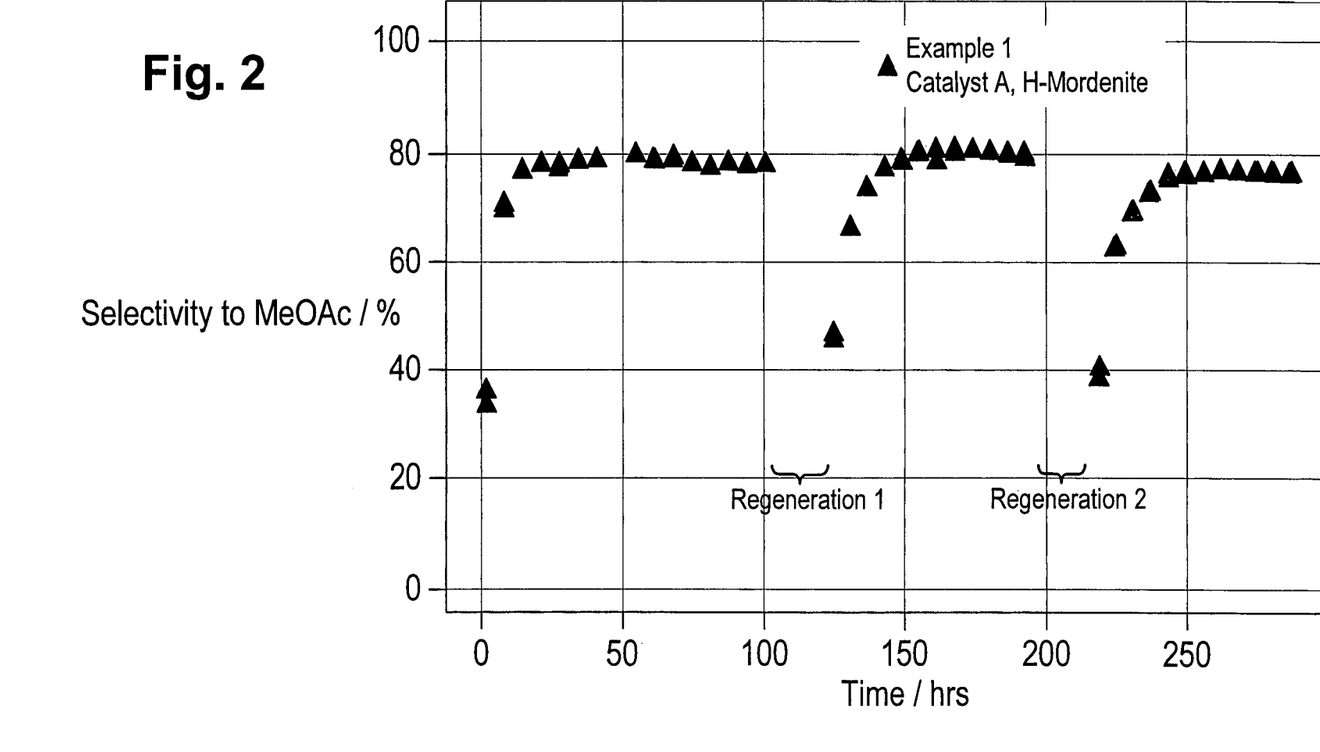
FIG. 2 depicts Selectivity to methyl acetate product versus time on stream for H-mordenite catalyst before and after regeneration at 400° C. with hydrogen.
Figure 3:
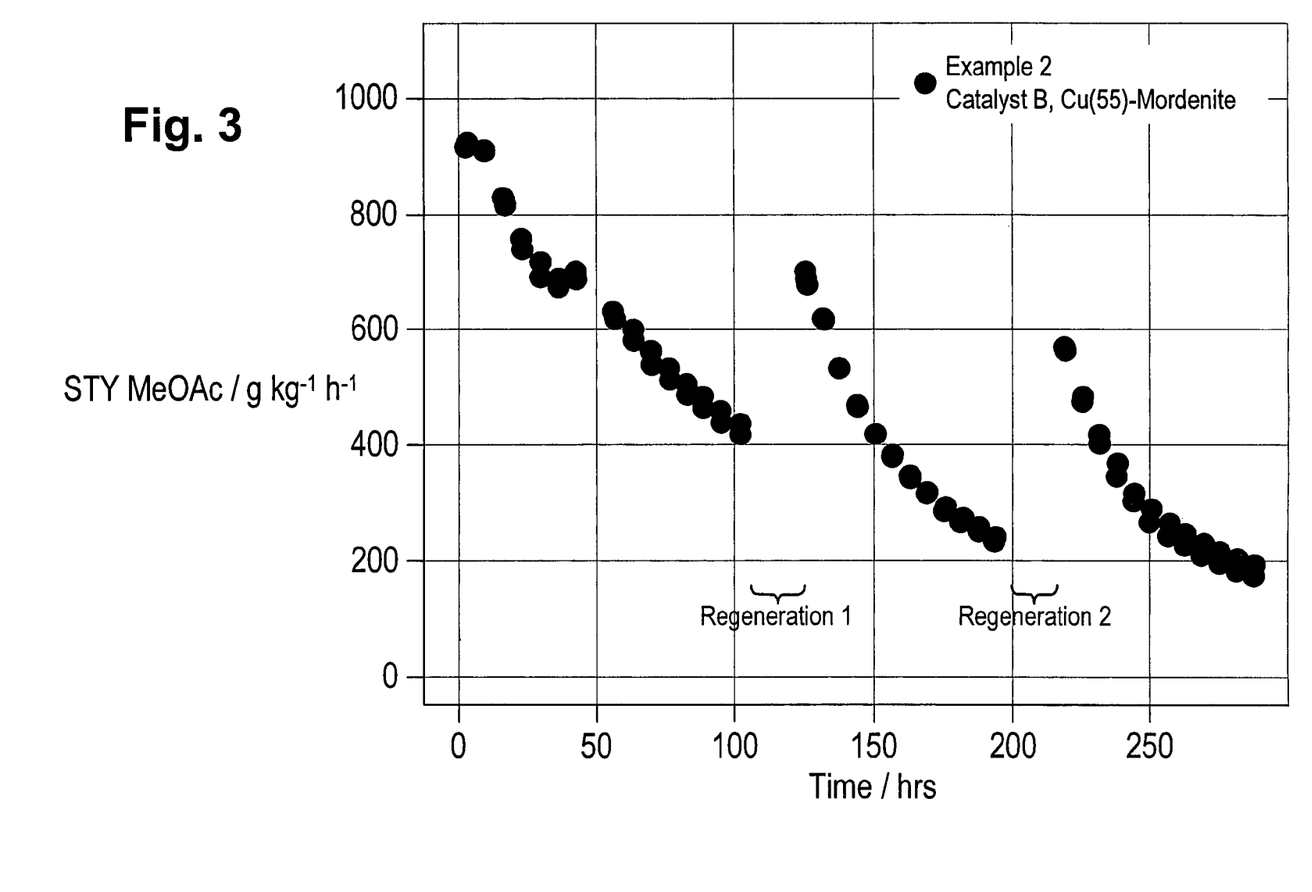
FIG. 3 depicts the STY to methyl acetate product in g $kg^{-1}$ $h^{-1}$ versus time on stream for Cu-mordenite catalyst before and after regeneration at 400° C.
Figure 4:
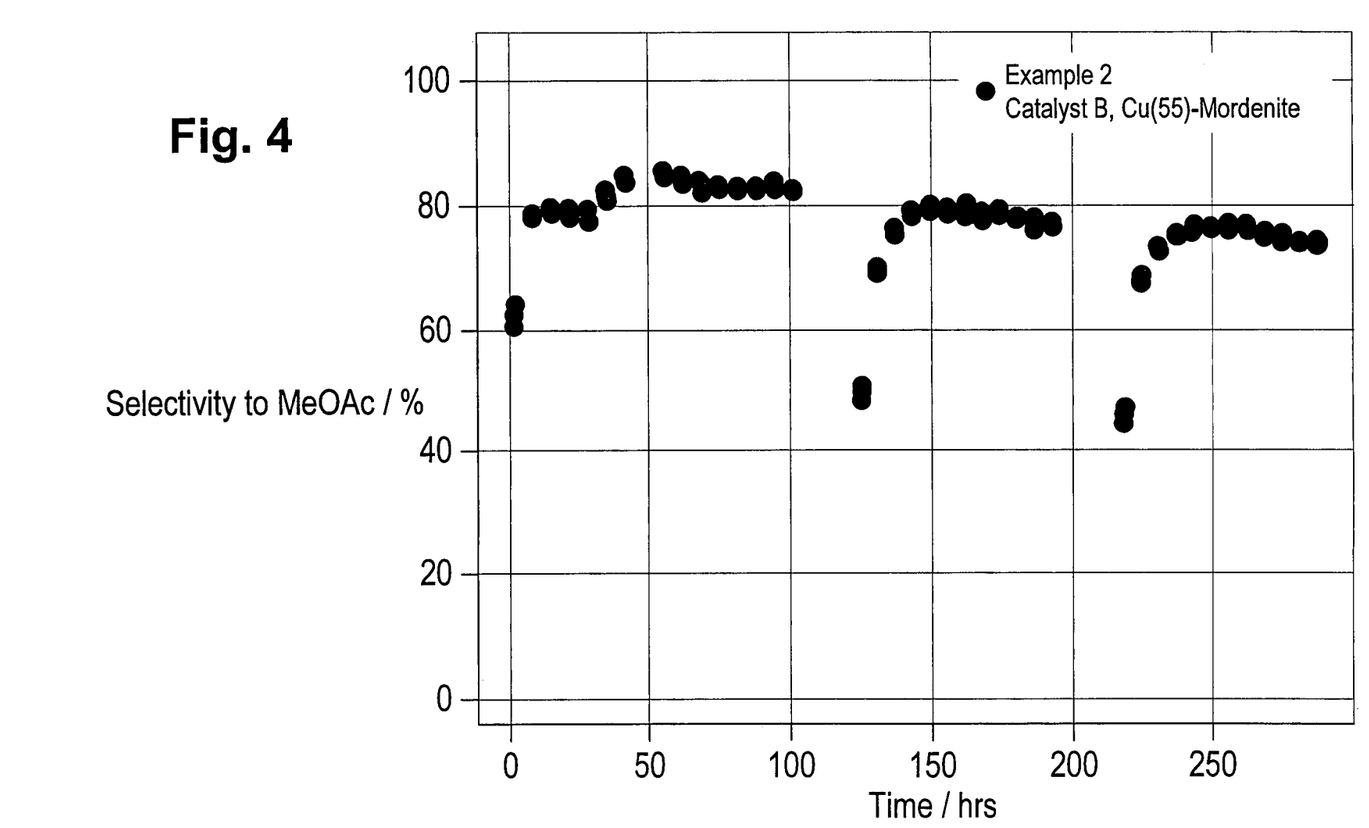
FIG. 4 depicts Selectivity to methyl acetate product versus time on stream for Cu-mordenite catalyst before and after regeneration at 400° C. with hydrogen.

The results for Examples 1 and 2 are shown in FIGS. 1 to 4. FIGS. 1 and 2 show that the carbonylation activity of H-mordenite can be largely restored by treatment with $H_2$ whilst substantially maintaining selectivity. FIGS. 3 and 4 demonstrate that the carbonylation activity of copper mordenite can be at least partially restored by treatment with $H_2$ whilst substantially maintaining selectivity.

EXAMPLES 3 TO 5

Preparation of Catalyst C—Cu(55)-Mordenite

H-mordenite (80.1 g) with a silica to alumina ratio of 20 (ex Süd-Chemie) was weighed into a 1 litre round bottomed flask with a stirrer bar. 14.29 g of copper (II) nitrate hemipentahydrate was dissolved in a minimum amount of deionised water. This solution was then added to the mordenite along with sufficient deionised water to give a mobile slurry. The top of the flask was covered loosely and the flask left to stir overnight. The copper mordenite was then dried under reduced vacuum using a rotary evaporator before being dried in an oven at 90° C. for 1-2 hours. It was then calcined in a muffle oven (oven volume=18 L) under a static atmosphere of air at 500° C. for 3 hours after being heated at 90° C. for 2 hours and then at 110° C. for 2 hours. The copper mordenite was then compacted at 10 tonnes in a 13 mm die set using a pneumatic press and crushed and sieved to a particle size fraction of 125 to 160 microns. The mordenite had a copper loading of ca. 55 mole % relative to aluminium contained in the mordenite.

Preparation of Catalyst D—Ag(55)-Mordenite

Silver mordenite was prepared according to the procedure described above for copper mordenite except that 80.0 g of the H-mordenite was used and the copper salt was replaced by 10.47 g of silver (I) nitrate. The silver mordenite so prepared had a silver loading of ca. 55 mole % relative to aluminium contained in the mordenite.

Preparation of Catalyst E—H-Mordenite

H-mordenite with a silica to alumina ratio of 20 (ex Süd-Chemie) was calcined compacted, crushed and sieved in accordance with the procedures described above in the preparation of copper mordenite.

Regeneration with Hydrogen and Carbon Monoxide in the Carbonylation of Dimethyl Ether Each of Catalysts C, D and E was used to catalyse the carbonylation of dimethyl ether with carbon monoxide. The apparatus and experimental procedure of General Reaction Method 1 was used except that dimethyl ether was fed as a vapour at a flow rate of 0.21 l/h to obtain a CO/H$_2$/DME molar ratio in the total feed of 75.8/19.0/5.2. The carbonylation reaction was allowed to continue for 100 hours under conditions of 300° C., 70 bar, a gas hourly space velocity (GHSV) of 4100 h$^{-1}$ and a CO/H$_2$/DME molar ratio in the total feed of 75.8/19.0/5.2. After 100 hours the regeneration with hydrogen and carbon monoxide was carried out as follows:

The CO/H$_2$/DME feed was changed to carbon monoxide and hydrogen with a molar ratio of 4:1, a GHSV of 4100 h$^{-1}$ and a total pressure of 70 bar. Whilst contacting the catalyst with the regenerating gas the temperature was increased from 300° C. to 400° C. at 1° C./min followed by a dwell time at 400° C. for 10 hours. After which time the reactors were cooled to 300° C. using N$_2$ fed at a GHSV of 4100 h$^{-1}$.

At 120 hours the carbonylation reaction was re-started under conditions of 300° C., 70 bar total pressure and a GHSV of 4100 h$^{-1}$ and a CO/H$_2$/DME molar ratio of 76.0/19.0/5.0. The reaction was then allowed to continue for a further 50 hours. The results for Examples 3 to 5 are given in Table 1.

TABLE 1

| Example and Catalyst Status | Catalyst | Time/ hours | MeOAc STY/ g kg$^{-1}$ h$^{-1}$ | Selectivity to MeOAc*/% |
|---|---|---|---|---|
| Example 3 | Cu-mordenite (Catalyst C) | | | |
| Before regeneration | | 8.9 | 1017 | 91 |
| | | 94.3 | 750 | 92 |
| After regeneration | | 127.6 | 964 | 92 |
| Example 4 | Ag-mordenite (Catalyst D) | | | |
| Before regeneration | | 2.0 | 940 | 87 |
| | | 8.5 | 846 | 92 |
| | | 93.9 | 406 | 92 |
| After regeneration | | 120.7 | 905 | 91 |
| Example 5 | H-mordenite (Catalyst E) | | | |
| Before regeneration | | 5.1 | 657 | 88 |
| | | 97.0 | 140 | 88 |
| After regeneration | | 123.7 | 338 | 90 |

*Selectivity to MeOAc based upon DME converted.

Table 1 shows that before regeneration the carbonylation activity of all the catalysts declines with time on stream, indicating deactivation of the catalyst had occurred. Examples 3 and 4 show that the activity of Cu-mordenite and Ag-mordenite can be substantially restored by regeneration with hydrogen and carbon monoxide and that after regeneration the high selectivity of the catalysts to MeOAc is maintained. Example 5 shows that the activity of H-mordenite can be at least partially restored by regeneration with hydrogen and carbon monoxide and that after regeneration the high selectivity of the catalyst to MeOAc is maintained.

EXAMPLE 6

Preparation of Catalyst F—H-Mordenite

H-mordenite with a silica to alumina ratio of 20 (ex Süd-Chemie) was calcined in a muffle oven (oven-volume=18 L) under a static atmosphere of air. The temperature was increased from room temperature to 90° C. at a ramp rate of ca. 3° C./min and then held at this temperature for 2 hours. The temperature was then increased to 110° C. at a ramp rate of ca. 1° C./min and held at this temperature for 2 hours before finally being increased to a temperature of 500° C. at a ramp rate of ca. 3° C./min and held at this temperature for 5 hours. The H-mordenite was then compacted at 12 tonnes in a 33 mm die set using a Specac Press, and then crushed and sieved to a particle size fraction of 212 to 335 microns.

Preparation of Catalyst G—Cu-(Ga)-Mordenite

NH$_4$-(Ga) Mordenite (0.5 g) with a SiO$_2$ to combined Ga$_2$O$_3$ and Al$_2$O$_3$ ratio of 19.4 and a Ga$_2$O$_3$:Al$_2$O$_3$ ratio of 1.5 (ex SINTEF) was weighed into a 5 mL phial and 755 microlitres of water added. 345 microlitres of a solution of copper (II) nitrate hemipentahydrate (98% ACS) having a concentration of 0.3 g/litre was then added. The phial was sealed and left to stir overnight. The material was then dried under reduced vacuum before being dried in an oven at 100° C. for 12 hours. The mordenite was then calcined in a muffle oven (oven volume=30 L) under a static atmosphere of air. The temperature was increased from room temperature to 500° C. at a ramp rate of 2° C./min and held at this temperature for 2 hours. The mordenite was then compacted at 12 tonnes in a 33 mm die set using a Specac Press, and then crushed and sieved to a particle size fraction of 212 to 335 microns. The mordenite so prepared had a copper loading of approximately 55 mole % of the combined amount of aluminium and gallium in the mordenite.

Regeneration with Hydrogen in the Carbonylation of Dimethyl Ether

Figure 5:
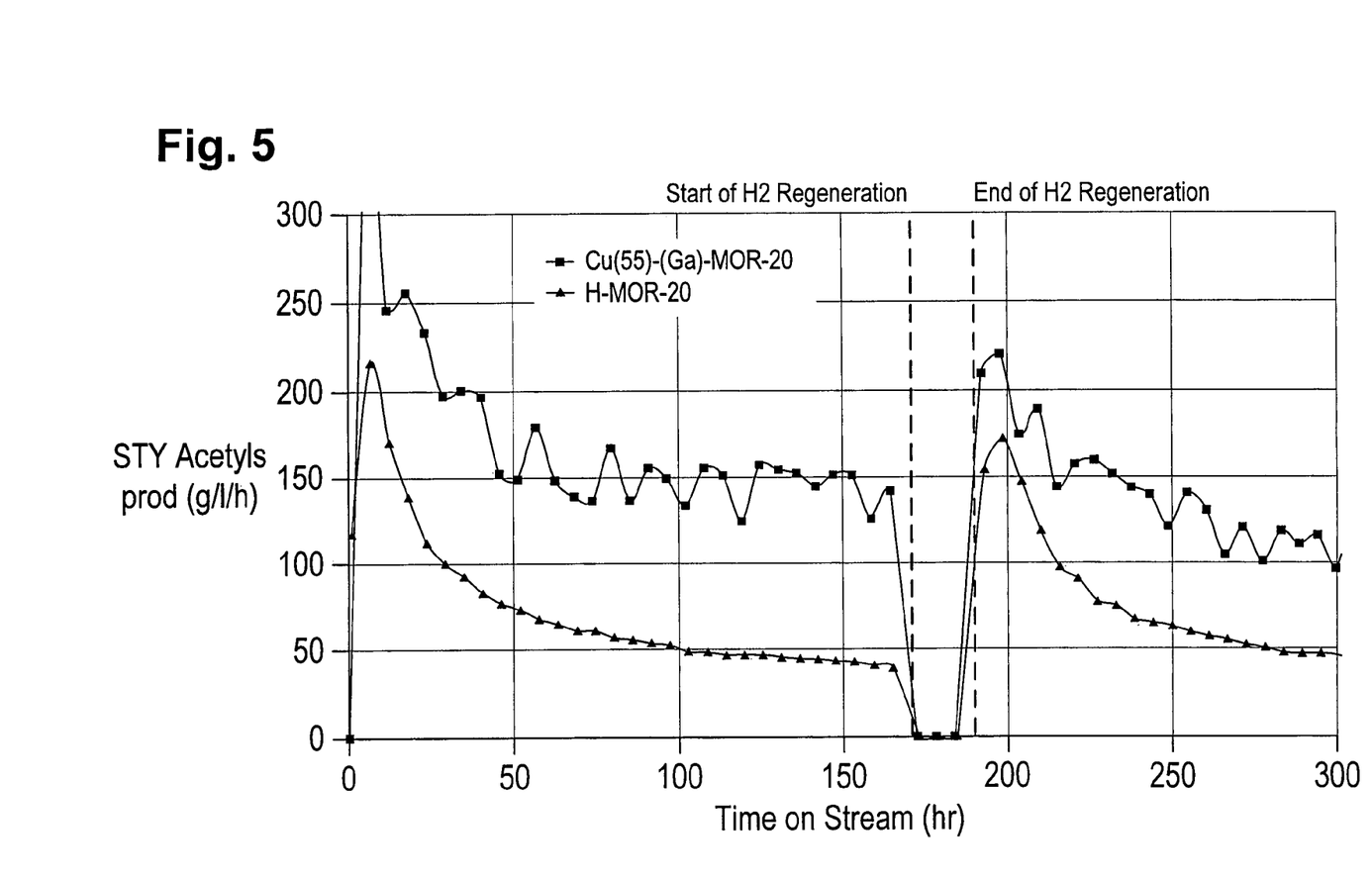
FIG. 5 depicts the STY to acetyls products in g $l^{-1}$ $h^{-1}$ versus time on stream for H-mordenite and Cu/Ga mordenite catalysts before and after regeneration at 300° C. with hydrogen.
Figure 6:
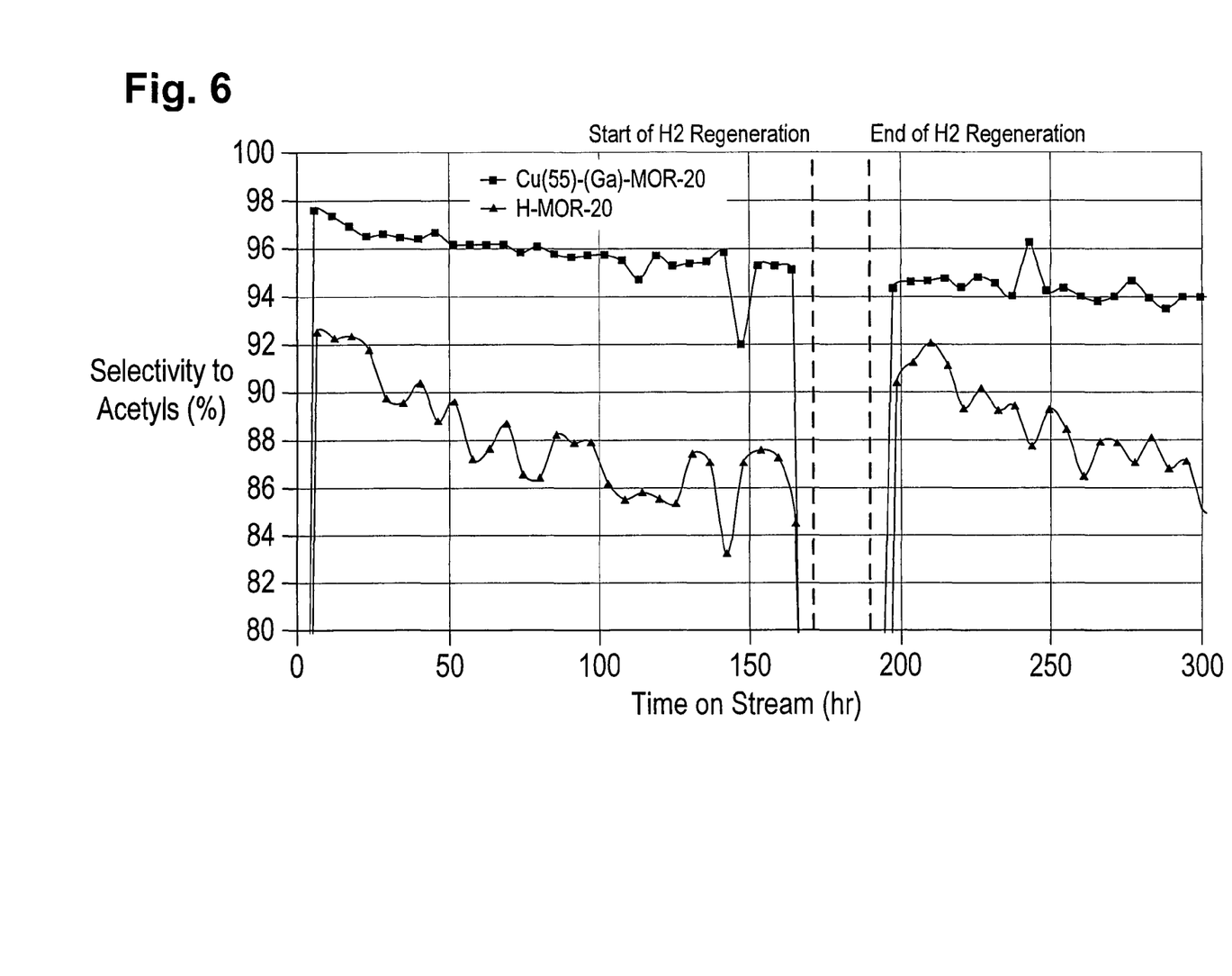
FIG. 6 depicts Selectivity to acetyls products in g $l^{-1}$ $h^{-1}$ versus time on stream for H— mordenite and Cu/Ga mordenite catalysts before and after regeneration at 300° C. with hydrogen.

The carbonylation of dimethyl ether was carried out in a pressure flow reactor unit consisting of 60 identical parallel isothermal co-current tubular reactors of the type described in, for example, WO2006107187. The reactors were arranged in 4 blocks of 15 reactors, each block having an independent temperature control. 50 micro litre samples of catalyst F or G (designed to give a GHSV of 4000 hr$^{-1}$) were loaded onto a metal sinter having a pore size of 20 micrometers. The catalyst samples were heated at a ramp rate of 5° C./min. to 100° C. at atmospheric pressure under 98.6 mol % nitrogen and 1.4 mol % helium at a flow rate of 3.4 ml/min, and held at this temperature for 1 hour. The reactors were each pressurised to 70 barg with 98.6 mole % nitrogen and 1.4 mole % helium and the system held at this condition for 1 hour. The gas feed was then changed to 63.1 mole % carbon monoxide, 15.8 mole % hydrogen, 19.7 mole % nitrogen and 1.4 mole % helium at a gas flow rate of 3.4 ml/min, and heated at a ramp rate 3° C./min. to a temperature of 300° C. The system was then held at this condition for 190 minutes. At this point activation of the catalysts was considered completed and the gas feed was changed to 63.1 mole % carbon monoxide, 15.8 mole % hydrogen, 14.8 mole % nitrogen, 1.4 mole % helium and 4.9 mole % dimethyl ether at a gas flow rate of 3.4 ml/min. After 170.7 hours, regeneration of the catalysts with hydrogen was carried out in the following manner. The carbonylation gas feed was changed to 78.9 mole % hydrogen, 19.7 mole % nitrogen and 1.4 mole % helium at a gas flow rate of 3.4 ml/min, and the reactors heated to 500° C. at a ramp rate of 2° C./min. Regeneration was allowed to continue at 500° C. for ca. 19 hours. The reactors were then cooled to 300° C. and the system was held under these conditions for 30 minutes before the carbonylation reaction was resumed by changing the gas feed to 63.1 mole % carbon monoxide, 15.8 mole % hydrogen, 14.8 mole % nitrogen, 1.4 mole % helium and 5 mole % dimethyl ether at a gas flow rate of 3.4 ml/min. The exit stream from the reactors was passed to two gas chromatograph, a Varian 4900 micro GC with three columns (Molecular sieve 5A, Porapak® Q, and CP-Wax-52) each column equipped with a thermal conductivity detector and an Interscience Trace GC with two columns (CP-Sil 5 and CP-Wax 52) each equipped with a flame ionisation detector. Catalyst activity (STY) and selectivity results are shown in FIGS. 5 and 6 respectively. In FIG. 5, $STY_{acetyls}$ is defined as the STY for the production of acetic acid (AcOH) plus the STY for the production of methyl acetate (MeOAc) multiplied by $MW_{AcOH}/MW_{MeOAc}$. In FIG. 6, selectivity is defined as the molar selectivity of the reaction of the methoxy group in the dimethyl ether (DME) feed to the products acetic acid and methyl acetate. Selectivity=([MeOAc]out+[AcOH]out)/ ([DME]in−[DME]out−0.5*[MeOH]out−0.5*[MeOAc]out) *100

FIG. 5 shows that the activity of the catalysts has been significantly increased after carrying out the hydrogen regeneration compared to the activity of the catalysts immediately before carrying out the regeneration. FIG. 6 shows that the regeneration has not caused any substantial loss in selectivity. The selectivity after regeneration of the Cu-(Ga)-MOR-20 (Catalyst G) is greater than that immediately before regeneration, while for the H-MOR-20 catalyst (Catalyst F), the selectivity after regeneration is within 1-2% of the selectivity immediately before regeneration.

EXAMPLE 7

Preparation of Catalyst H—Cu(55)-Mordenite

H-Mordenite (500 g) with a silica to alumina ratio of 20 (CBV21A ex Zeolyst) and 90.5 g of copper (II) nitrate hemipentahydrate (98% ACS) were weighed into a 4 L round bottomed flask fitted with a stirrer. Sufficient deionised water (ca. 2 L) was added to the flask to obtain a thick slurry. The top of the flask was loosely covered and the flask left to stir overnight. The copper mordenite was then dried under reduced vacuum using a rotary evaporator before being dried in an oven at 90° C. for 1 hour. The dried copper mordenite was then calcined according to the procedure used in the preparation of catalyst G. The calcined copper mordenite was then compacted at 12 tonnes in a 33 mm die set using a Specac Press, and crushed and sieved to a particle size fraction of 250 to 500 microns. The mordenite had a copper loading of 55 mole % relative to aluminium contained in the mordenite.

Preparation of Catalyst I—Ag(55)-Mordenite

Silver mordenite was prepared according to the method described above for Catalyst H except that 120 g of the H-mordenite was used and the copper salt was replaced by 15.7 g of silver nitrate (99% ACS reagent grade). The silver mordenite so prepared had a silver loading of 55 mol % relative to aluminium contained in the mordenite.
Regeneration with Hydrogen and Carbon Monoxide in the Carbonylation of Dimethyl Carbonate.

Each of Catalysts H and I was used to carbonylate dimethyl carbonate with carbon monoxide in the presence of hydrogen. Each carbonylation reaction was carried out on a pressure flow reactor unit comprising 16 reactors. Four Hastelloy reactor tubes with an integral electrical heating jacket were each packed with 0.6 ml of Catalyst H and 0.2 g of a gamma alumina pre-bed and four Hastelloy reactor tubes were each packed with 0.6 ml of Catalyst I and 0.2 g of a gamma alumina pre-bed. The reactors and heating jacket were installed on the unit in a heated cabinet. The system was designed so that the temperature of a catalyst bed is controlled by the integral heating jacket while the temperature of the pre-bed is controlled by the heated cabinet. Initially the reactors were heated at atmospheric pressure under a flow of nitrogen to 130° C. in the heated cabinet, which was then maintained at this temperature. The feed gas was then changed to 80 mole % carbon monoxide and 20 mole % hydrogen and the system was pressurised to 20 barg. The gas flow rate (GHSV) of these and subsequent steps was 5000 hr$^{-1}$. During this time the reactors were heated to 300° C. at a ramp rate of 3° C. per minute using the electrical heating jacket and the system was held under these conditions for two hours. The carbonylation reaction was then started by feeding dimethyl carbonate at a rate designed to give a gas feed comprising 76 mole % carbon monoxide, 19 mole % hydrogen and 5 mole % dimethyl carbonate. The reaction was run under these conditions for ca. 68 hours. The catalysts were then regenerated at 4 different temperatures using a gas containing a 1:1 mixture of carbon monoxide and hydrogen using the following regeneration procedure. The dimethyl carbonate feed was ceased and a regenerating gas comprising 50 mole % carbon monoxide and 50 mole % hydrogen was introduced into each reactor. The temperatures in the 4 reactors containing Catalyst H were adjusted to 275, 300, 325 and 350° C. Similarly the temperatures in the 4 reactors containing Catalyst I were altered to 275, 300, 325 and 350° C. The system was maintained under these conditions for ca. 27 hours. Over the following 16 hours the gas feed was adjusted to 80 mole % carbon monoxide and 20 mole % hydrogen. The temperature of each of the reactors was then adjusted to 300° C. and the carbonylation reaction was re-started using dimethyl carbonate at a rate designed to give a gas feed of 76 mole % carbon monoxide, 19 mole % hydrogen and 5 mole % dimethyl carbonate. During the reactions a constant flow of reaction off-gases was taken from the high pressure side of the reactor system through a needle valve, let down to atmospheric pressure at a temperature of at least 130° C. and passed to a gas chromatograph for analysis. The space time yield (STY) to methyl acetate and acetic acid products obtained in the carbonylation reactions just before regeneration (66-68 hours) and just after regeneration (109-112 hours) are given in Tables 2 and 3 below. Table 2 provides STY data obtained using Catalyst H (copper mordenite) and Table 3 provides STY data obtained using Catalyst I (silver mordenite).

TABLE 2

Copper Mordenite catalyst

| Regeneration Temperature ° C. | STY before regeneration g/l/hr | STY after regeneration g/l/hr |
|---|---|---|
| 275 | 364 | 366 |
| 300 | 381 | 409 |
| 325 | 376 | 400 |
| 350 | 374 | 436 |

TABLE 3

Silver Mordenite catalyst

| Regeneration Temperature ° C. | STY before regeneration g/l/hr | STY after regeneration g/l/hr |
|---|---|---|
| 275 | 197 | 188 |
| 300 | 199 | 236 |
| 325 | 204 | 278 |
| 350 | 180 | 281 |

The invention claimed is:
1. A process for the in-situ regeneration of a zeolite catalyst in a carbonylation process for the production of at least one of methyl acetate and acetic acid which process comprises the steps of:

(a) contacting a carbonylatable reactant selected from methanol, dimethyl ether and dimethyl carbonate and carbon monoxide in a reactor with a zeolite catalyst and recovering a product stream comprising at least one of methyl acetate and acetic acid from said reactor;

(b) ceasing contact of the catalyst with the carbonylatable reactant;

(c) regenerating the catalyst with a regenerating gas selected from hydrogen or a mixture of hydrogen and carbon monoxide at a temperature in the range 250 to 600° C.;

(d) terminating the hydrogen regenerating step and resuming contact of the catalyst with the carbonylatable reactant and carbon monoxide.

2. The process according to claim 1 wherein the zeolite catalyst is a mordenite.

3. The process according to claim 1 wherein the regenerating gas is a mixture of carbon monoxide and hydrogen and the molar ratio of carbon monoxide:hydrogen is in the range 1:20 to 10:1.

4. The process according to claim 1 wherein the regeneration is carried out at a temperature is in the range 300 to 500° C.

5. The process according to claim 1 wherein the regeneration is carried out at a total pressure in the range 1 to 100 bar.

6. The process according to claim 1 wherein hydrogen is used as the regenerating gas in the absence of carbon monoxide and the hydrogen partial pressure is in the range 5 to 80 bar.

7. The process according to claim 1 wherein a mixture of hydrogen and carbon monoxide is used as the regenerating gas and wherein the hydrogen partial pressure is in the range 5 to 80 bar.

8. The process according to claim 1 wherein a mixture of hydrogen and carbon monoxide is used as the regenerating gas and wherein the carbon monoxide partial pressure is in the range 0.1 to 80 bar.

9. The process according to claim 8 wherein the carbon monoxide partial pressure is in the range 5 to 65 bar.

10. The process according to claim 1 wherein a mixture of hydrogen and carbon monoxide is used as the regenerating gas and wherein the hydrogen partial pressure is in the range 10 to 70 bar and the carbon monoxide partial pressure is in the range 5 to 65 bar.

11. The process according to claim 1 in which regeneration is carried out once and wherein during the regeneration the catalyst temperature is adjusted within a temperature in the range 250 to 600° C.

12. The process according to claim 1 wherein regeneration is carried out multiple times during the course of the carbonylation process and wherein in each regeneration the catalyst temperature is in the range 250 to 600° C.

13. The process according to claim 12 wherein a regeneration is carried out under the same or different regeneration conditions to those of a previous or subsequent regeneration.

14. The process according to claim 1 wherein the carbonylation process is carried out in the presence of hydrogen.

15. The process according to claim 1 wherein methyl acetate product is hydrolysed to acetic acid.

* * * * *